(12) United States Patent
Kang et al.

(10) Patent No.: US 12,019,139 B2
(45) Date of Patent: Jun. 25, 2024

(54) ELECTRONIC DEVICE AND METHOD USING UWB SIGNAL

(71) Applicant: Samsung Electronics Co., Ltd., Suwon-si (KR)

(72) Inventors: Moonseok Kang, Suwon-si (KR); Yi Yang, Suwon-si (KR); Hyunchul Kim, Suwon-si (KR); Jiho Shin, Suwon-si (KR); Sukgi Hong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 93 days.

(21) Appl. No.: 17/857,525

(22) Filed: Jul. 5, 2022

(65) Prior Publication Data

US 2023/0003866 A1 Jan. 5, 2023

Related U.S. Application Data

(63) Continuation of application No. PCT/KR2022/008076, filed on Jun. 8, 2022.

(30) Foreign Application Priority Data

Jul. 2, 2021 (KR) .................. 10-2021-0087256

(51) Int. Cl.
*G01S 13/08* (2006.01)
*H04B 1/7163* (2011.01)

(52) U.S. Cl.
CPC ............ *G01S 13/08* (2013.01); *H04B 1/7163* (2013.01)

(58) Field of Classification Search
CPC .......... G01S 13/06; G01S 13/08; H04B 1/69; H04B 1/692; H04B 1/70758; H04B 1/7163; H04J 2013/0085
USPC ......... 375/130, 131, 133, 141; 370/328–330, 370/334, 336, 337, 345, 347, 509, 510, 370/512; 455/456.1, 456.4, 456.5, 456.6
See application file for complete search history.

(56) References Cited

U.S. PATENT DOCUMENTS

| 7,423,576 B2 | 9/2008 | Sahinoglu et al. |
| 2006/0104198 A1 | 5/2006 | Takano |

(Continued)

FOREIGN PATENT DOCUMENTS

| JP | 2006-148457 A | 6/2006 |
| JP | 2021-089236 A | 6/2021 |

(Continued)

OTHER PUBLICATIONS

International Search Report dated Sep. 8, 2022, issued in International Application No. PCT/KR2022/008076.

*Primary Examiner* — Young T. Tse
(74) *Attorney, Agent, or Firm* — Jefferson IP Law, LLP

(57) ABSTRACT

An electronic device is provided. The electronic device includes an antenna module, a communication module configured to control the antenna module, and at least one processor operatively connected to the communication module, wherein the at least one processor transmits a ultra-wide band (UWB) signal including a first data frame, receives, based on the transmitted first data frame, a reflected first data frame, obtains a first channel impulse response by using the reflected first data frame, acquires information by using the channel impulse response, and receives a UWB signal including a second data frame from an external electronic device in response to the transmitted first data frame.

21 Claims, 19 Drawing Sheets

(56) References Cited

U.S. PATENT DOCUMENTS

| | | |
|---|---|---|
| 2008/0313304 A1* | 12/2008 | Kanda ................ H04N 1/00278 |
| | | 709/217 |
| 2018/0038949 A1 | 2/2018 | Cha et al. |
| 2019/0271776 A1 | 9/2019 | Davis et al. |
| 2020/0259522 A1 | 8/2020 | Hammerschmidt et al. |
| 2020/0297236 A1 | 9/2020 | Rimini et al. |
| 2020/0348406 A1 | 11/2020 | Jain et al. |
| 2020/0348409 A1 | 11/2020 | McLaughlin et al. |
| 2020/0366335 A1* | 11/2020 | Lee ...................... H04W 88/06 |
| 2020/0400806 A1 | 12/2020 | Choi et al. |
| 2021/0034160 A1 | 2/2021 | Hof et al. |
| 2021/0076350 A1* | 3/2021 | Yang ......................... G01S 3/50 |
| 2021/0091840 A1 | 3/2021 | Choi et al. |

FOREIGN PATENT DOCUMENTS

| | | |
|---|---|---|
| KR | 10-2018-0016820 A | 2/2018 |
| KR | 10-2020-0096803 A | 8/2020 |
| KR | 10-2020-0145066 A | 12/2020 |
| KR | 10-2021-0036152 A | 4/2021 |

\* cited by examiner

ELECTRONIC DEVICE AND METHOD USING UWB SIGNAL

CROSS-REFERENCE TO RELATED APPLICATION(S)

This application is a continuation application, claiming priority under § 365(c), of an International application No. PCT/KR2022/008076, filed on Jun. 8, 2022, which is based on and claims the benefit of a Korean patent application number 10-2021-0087256, filed on Jul. 2, 2021, in the Korean Intellectual Property Office, the disclosure of which is incorporated by reference herein in its entirety.

TECHNICAL FIELD

The disclosure relates to an electronic device and a method using an ultra-wide band (UWB) signal. More particularly, the disclosure relates to an electronic device and a method for using a UWB signal as a radar signal while using the same signal to measure a distance to an external device.

BACKGROUND ART

Ultra-wide band (UWB) signals may be used in short-range wireless communication using radio waves, such as Bluetooth or wireless fidelity (Wi-Fi). When measurement is made using a UWB signal in communication, errors in the distance and azimuth between devices can be reduced to 10 cm and 5 degrees or smaller. Since use of UWB signals can increase the accuracy of distance and azimuth in comparison with other signals, various services use UWB signals.

UWB signals may also be used as radar signals as well as for communication. When UWB signals are used as radar signals, the change in surrounding environment and the existence/absence of a living thing can be detected, the heart rate of the living thing can be identified, and the gesture thereof can also be recognized.

The above information is presented as background information only to assist with an understanding of the disclosure. No determination has been made, and no assertion is made, as to whether any of the above might be applicable as prior art with regard to the disclosure.

DISCLOSURE

Technical Problem

UWB signals may be used to measure distance in communication or used as radar signals, and may be used for only one purpose at a time. In a case where an electronic device uses UWB signals for communication to measure a distance to an external electronic device, the electronic device may be allowed to use UWB signals as radar signals only when distance is not measured. Therefore, it may be difficult to sufficiently secure a time required to use UWB signals as radar signals.

Aspects of the disclosure are to address at least the above-mentioned problems and/or disadvantages and to provide at least the advantages described below. Accordingly, an aspect of the disclosure is to provide an electronic device and a method for using a UWB signal as a radar signal while using the same signal to measure a distance to an external device.

Additional aspects will be set forth in part in the description which follows and, in part, will be apparent from the description, or may be learned by practice of the presented embodiments.

Technical Solution

In accordance with an aspect of the disclosure, an electronic device is provided. The electronic device includes an antenna module, a communication module configured to control the antenna module, and at least one processor operatively connected to the communication module, wherein the at least one processor is configured to transmit a ultra-wide band (UWB) signal including a first data frame, receive, based on the transmitted first data frame, a reflected first data frame, obtains a first channel impulse response by using the reflected first data frame, acquire information by using the channel impulse response, and receive a UWB signal including a second data frame from an external electronic device in response to the transmitted first data frame.

In accordance with another aspect of the disclosure, a method of operating an electronic device is provided. The method includes transmitting a ultra-wide band (UWB) signal including a first data frame, receiving, based on the transmitted first data frame, a reflected first data frame, obtaining a first channel impulse response by using the reflected first data frame, acquiring information by using the channel impulse response, and receiving a UWB signal including a second data frame from an external electronic device in response to the transmitted first data frame.

Advantageous Effects

According to various embodiments of the disclosure, an electronic device may use UWB signals to measure a distance to an external electronic device, and also use the UWB signals as radar signals at the same time.

Other aspects, advantages, and salient features of the disclosure will become apparent to those skilled in the art from the following detailed description, which, taken in conjunction with the annexed drawings, discloses various embodiments of the disclosure.

DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
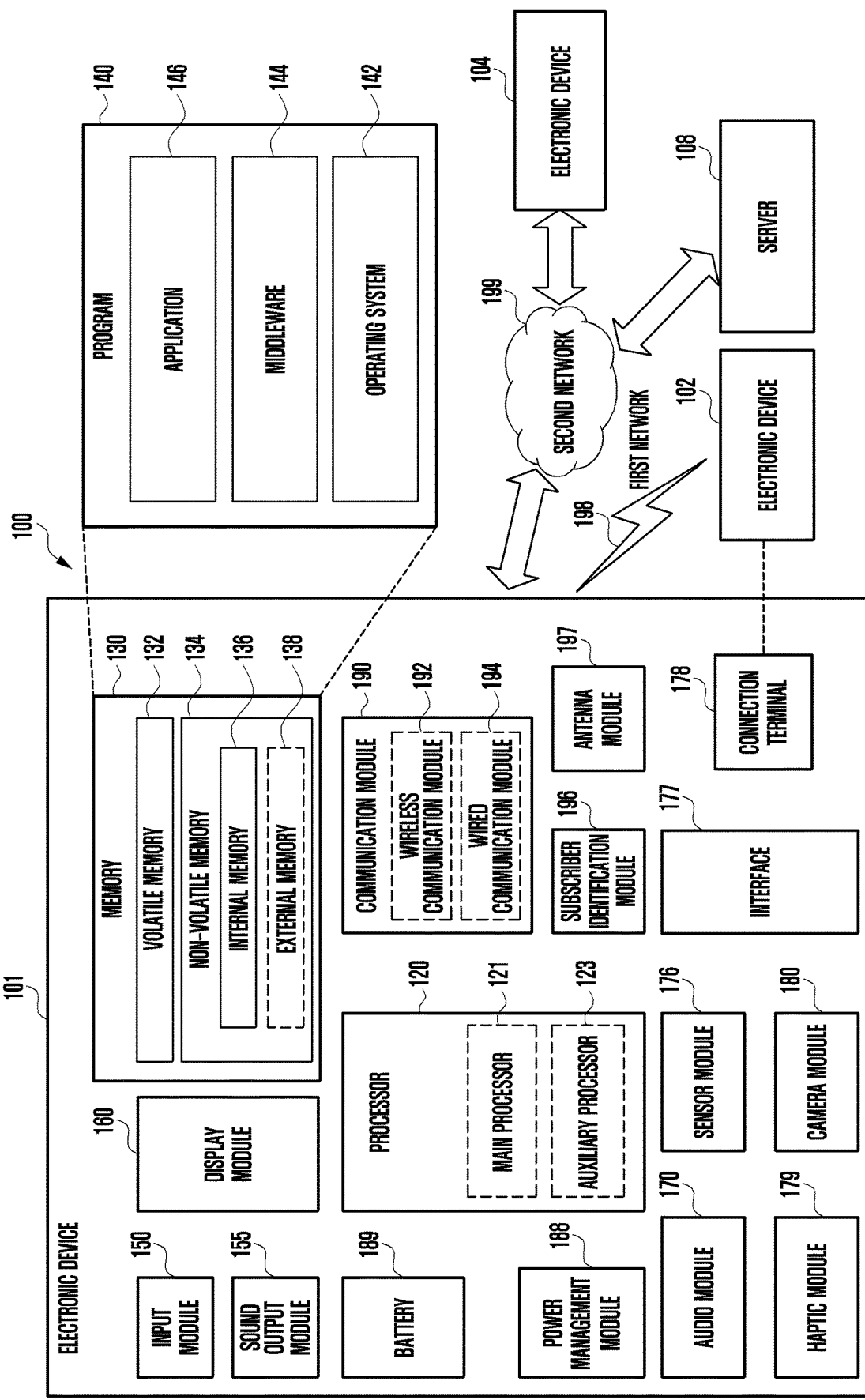
FIG. 1 is a block diagram of an electronic device in a network environment according to an embodiment of the disclosure.

FIG. 1 is a block diagram illustrating an electronic device in a network environment according to an embodiment of the disclosure.

Referring to FIG. 1, an electronic device 101 in a network environment 100 may communicate with an external electronic device 102 via a first network 198 (e.g., a short-range wireless communication network), or at least one of an external electronic device 104 or a server 108 via a second network 199 (e.g., a long-range wireless communication network). According to an embodiment of the disclosure, the electronic device 101 may communicate with the external electronic device 104 via the server 108. According to an embodiment of the disclosure, the electronic device 101 may include a processor 120, a memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments of the disclosure, at least one of the components (e.g., the connecting terminal 178) may be omitted from the electronic device 101, or one or more other components may be added in the electronic device 101. In some embodiments of the disclosure, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment of the disclosure, as at least part of the data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment of the disclosure, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., a sleep) state, or together with the main processor 121 while the main processor 121 is in an active state (e.g., executing an application). According to an embodiment of the disclosure, the auxiliary processor 123 (e.g., an image signal processor or a communication processor) may be implemented as part of another component (e.g., the camera module 180 or the communication module 190) functionally related to the auxiliary processor 123. According to an embodiment of the disclosure, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment of the disclosure, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment of the disclosure, the display module 160 may include a touch sensor adapted to detect a touch, or a pressure sensor adapted to measure the intensity of force incurred by the touch.

The audio module 170 may convert a sound into an electrical signal and vice versa. According to an embodiment of the disclosure, the audio module 170 may obtain the sound via the input module 150, or output the sound via the sound output module 155 or a headphone of an external electronic device (e.g., an external electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment of the disclosure, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the external electronic device 102) directly (e.g., wiredly) or wirelessly. According to an embodiment of the disclosure, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the external electronic device 102). According to an embodiment of the disclosure, the connecting terminal 178 may include, for example, a HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 179 may include, for example, a motor, a piezoelectric element, or an electric stimulator.

The camera module 180 may capture a still image or moving images. According to an embodiment of the disclosure, the camera module 180 may include one or more lenses, image sensors, image signal processors, or flashes.

The power management module 188 may manage power supplied to the electronic device 101. According to one embodiment of the disclosure, the power management module 188 may be implemented as at least part of, for example, a power management integrated circuit (PMIC).

The battery 189 may supply power to at least one component of the electronic device 101. According to an embodiment of the disclosure, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the external electronic device 102, the external electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment of the disclosure, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5th generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4th generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter wave (mmWave) band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the external electronic device 104), or a network system (e.g., the second network 199). According to an embodiment of the disclosure, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment of the disclosure, the antenna module 197 may include an antenna including a radiating element composed of a conductive material or a conductive pattern formed in or on a substrate (e.g., a printed circuit board (PCB)). According to an embodiment of the disclosure, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment of the disclosure, another component (e.g., a radio frequency integrated circuit (RFIC)) other than the radiating element may be additionally formed as part of the antenna module 197.

According to various embodiments of the disclosure, the antenna module 197 may form a mmWave antenna module. According to an embodiment of the disclosure, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment of the disclosure, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment of the disclosure, the external electronic device 104 may include an internet-of-things (IoT) device. The server 108 may be an intelligent server using machine learning and/or a neural network. According to an embodiment of the disclosure, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
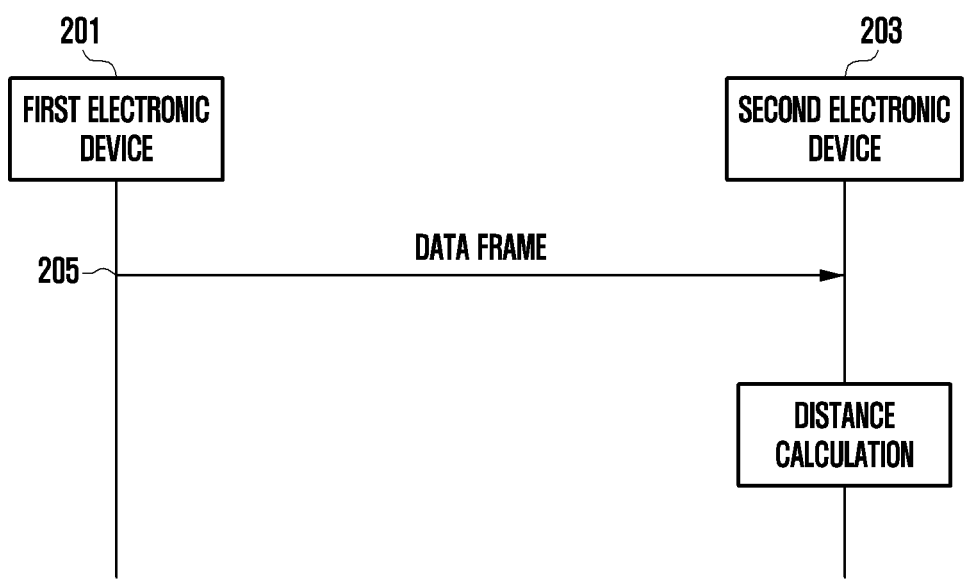
FIGS. 2A, 2B, and 2C are diagrams illustrating in brief a ranging method using UWB signals according to various embodiments of the disclosure.
Figure 2B:
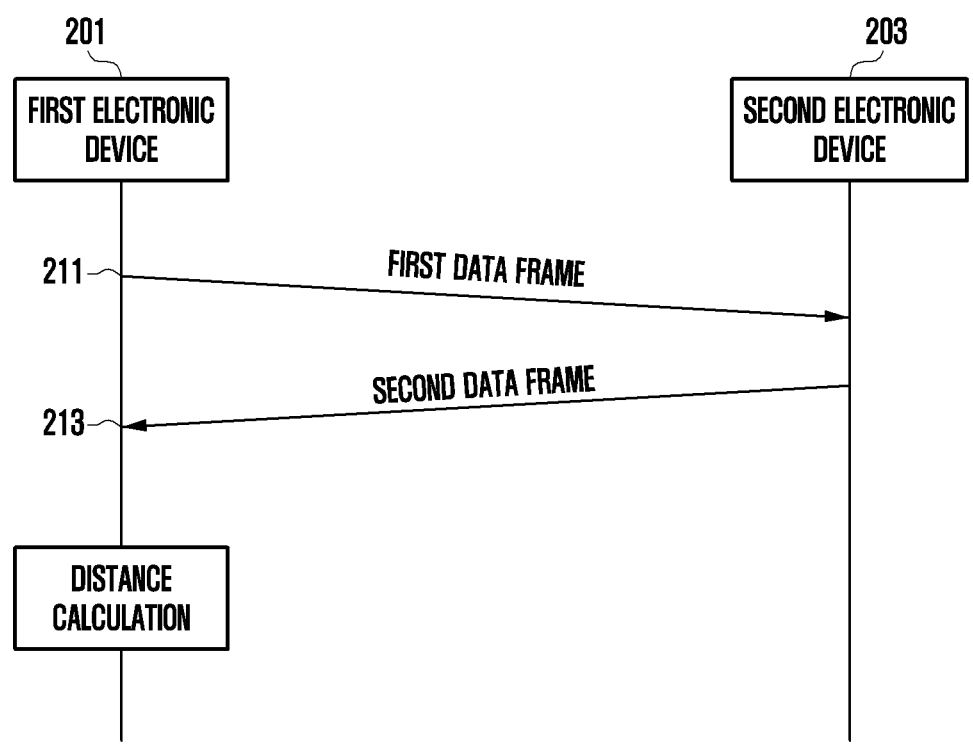
Figure 2C:
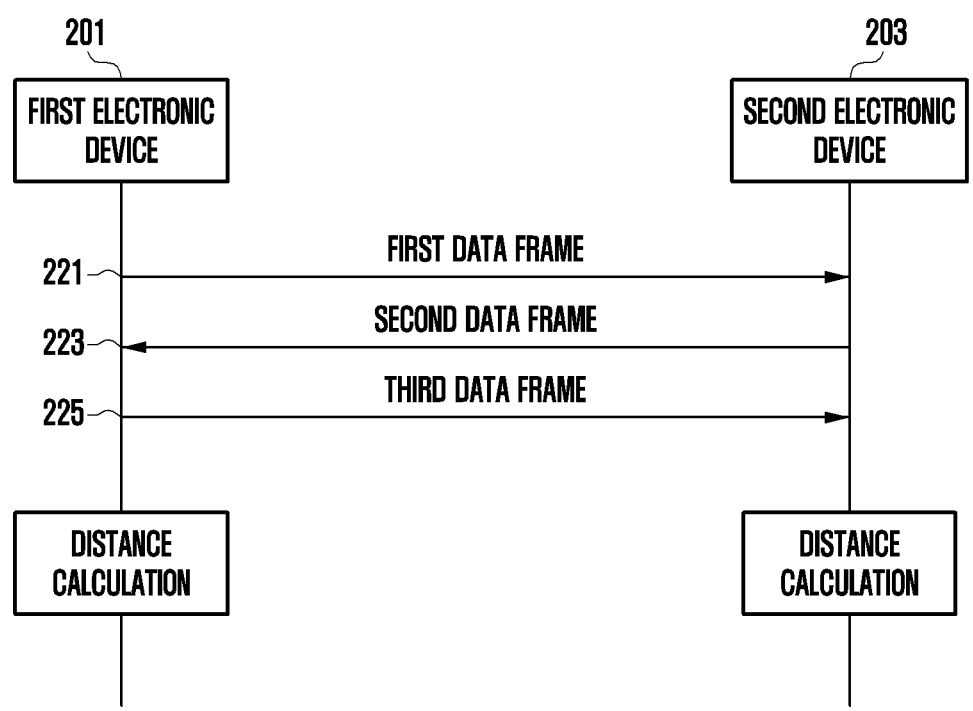

FIGS. 2A, 2B, and 2C are diagrams illustrating in brief a ranging method using UWB signals (UWB ranging method) according to various embodiments of the disclosure.

According to various embodiments of the disclosure, an inter-device ranging method using UWB signals may be classified into a one way ranging method and a two way ranging method. FIG. 2A illustrates the one way ranging method, and FIGS. 2B and 2C illustrate the two way ranging method.

Referring to FIG. 2A, the one way ranging method is a method in which, when a first electronic device 201 transmits a data frame including transmission time information to a second electronic device 203 (as indicated by reference numeral 205), the second electronic device 203 identifies a reception time of the data frame, and calculates a distance to the first electronic device 201, based on the transmission time information included in the data frame. The one way ranging method may require little time to measure distance and small power consumption because communication is performed only one time. However, the same method can be applied only when the first electronic device 201 and the second electronic device 203 are synchronized.

According to various embodiments of the disclosure, the two way ranging method is a method in which the first electronic device and the second electronic device transmit or receive signals several times to share time information owned thereby and thus measure the distance therebetween, based on a reduced time error. The two way ranging method may require large power consumption and take long time to measure distance. However, the same method can be used even when the first electronic device and the second electronic device are not synchronized. The two way ranging method may be classified into a single-side two way ranging method (SS-TWR) and a double-side two way ranging method (DS-TWR). FIG. 2B illustrates a single-side two way ranging method, and FIG. 2C illustrates a double-side two way ranging method.

Referring to FIG. 2B, the single-side two way ranging method is a method in which, when the first electronic device 201 transmits a first data frame (as indicated by reference numeral 211), the second electronic device 203 transmits a second data frame 213 including a reception time of the first data frame 211 and a transmission time of a data frame by the second electronic device (as indicated by reference numeral 213), and the first electronic device 201 calculates the distance between the first electronic device 201 and the second electronic device 203 by further using information included in the received second data frame 213.

Referring to FIG. 2C, the double-side two way ranging method is a method in which, when the first electronic device 201 transmits a first data frame (as indicated by reference numeral 221), the second electronic device 203 transmits a second data frame 223 including a reception time of the first data frame and a transmission time of the second data frame (as indicated by reference numeral 223), and the first electronic device 201 transmits again, to the second electronic device 203, a third data frame including a reception time of the second data frame and a transmission time of the third data frame (as indicated by reference numeral 225) so that the first electronic device 201 and the second electronic device 203 can all measure the distance therebetween.

Figure 3:
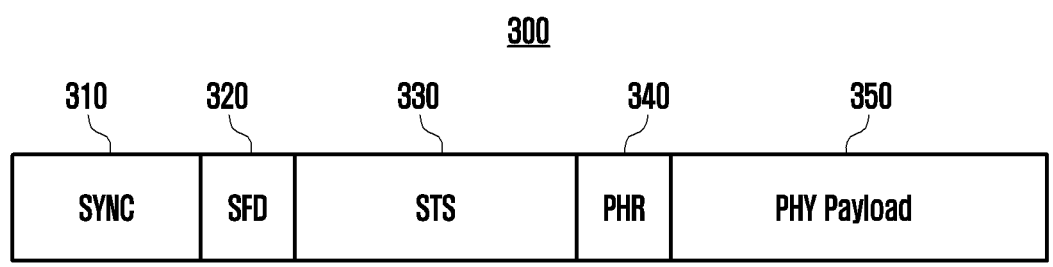
FIG. 3 illustrates a data frame structure which may be included in a UWB signal according to an embodiment of the disclosure.

FIG. 3 illustrates a data frame structure which may be included in a UWB signal according to an embodiment of the disclosure.

Referring to FIG. 3, a data frame 300 transmitted by an electronic device (e.g., the electronic device 101 in FIG. 1) to measure a distance may include a synchronizer (SYNC) 310, a start of frame delimiter (hereinafter, "SFD") 320, a scrambled timestamp secure (hereinafter, "STS") 330, a physical (PHY) header (hereinafter, PHR) 340, and a PHY payload 350.

According to various embodiments of the disclosure, the SYNC 310 may include data for temporal synchronization between an electronic device (e.g., the first electronic device 201 in FIGS. 2A to 2C) and an external electronic device (e.g., the second electronic device 203 in FIGS. 2A to 2C), and the SFD 320 may include data indicating the end of the SYNC 310 and the start of the PHR 340. The STS 330 may include data implemented to prevent attack (e.g., relay attack) against data. The PHR 340 may include a header of the PHY payload 350, and the PHY payload 350 may include data to be transmitted.

According to various embodiments of the disclosure, a UWB signal may be configured in a pulse type, and thus the electronic device may not only use UWB signals to recognize a distance to the external electronic device, but also use UWB signals as radar signals.

According to various embodiments of the disclosure, the electronic device 101 may select and use a part of the data frame 300 to use an UWB signal as a radar signal. For example, the electronic device 101 may select at least one of the SYNC 310, the SFD 320, the STS 330, the PHR 340, and the PHY payload 350 in the data frame 300, and use the selected one as a radar signal.

In the following description, the data frame described with reference to FIG. 3 is used as an example, but a person skilled in the art will understand that a data frame having a different structure included in an UWB signal may also be applied to the disclosure.

Figure 4:
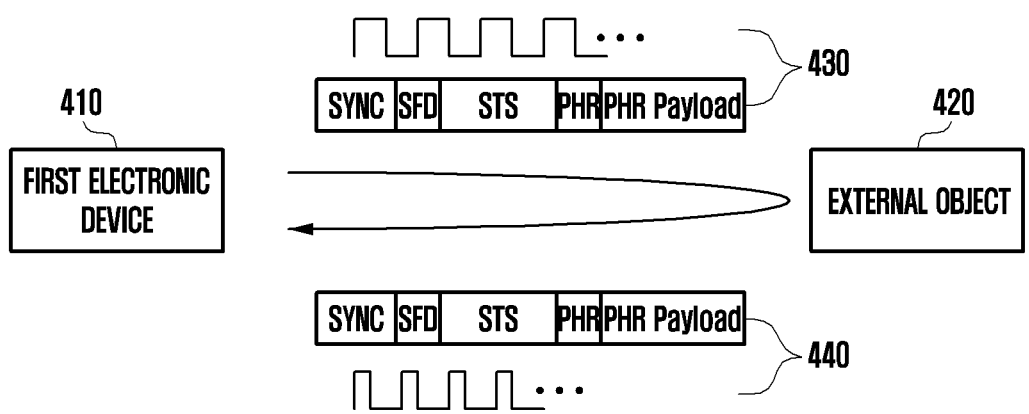
FIG. 4 is a diagram illustrates using UWB signals as radar signals according to an embodiment of the disclosure.

FIG. 4 is a diagram illustrates using UWB signals as radar signals according to an embodiment of the disclosure.

RADAR is an acronym of radio detection and ranging, and may indicate a technique of measuring detection and ranging by using radio waves, and radar signals may be signals used for detection and ranging.

Referring to FIG. 4, an electronic device 410 may transmit a UWB signal 430 including a data frame (e.g., the data frame 300 in FIG. 3). The UWB signal 430 may be received by an external object 420, or may be reflected by the external object 420. When a UWB signal 440 is reflected by the external object 420, the electronic device 410 may receive the reflected UWB signal 440. When the data frame 300 configured in a pulse type collides with the external object 420 and is reflected thereby, the pulse configuration thereof may be changed.

According to various embodiments of the disclosure, the electronic device 410 may receive the UWB signal 440 reflected by the external object 420, so as to recognize information, such as a distance, direction, and altitude related to the external object 420. The external object 420 may be an object, a person, or an animal configuring a surrounding environment of the electronic device 410, and may not be limited thereto. Information which the electronic device 410 may acquire from the UWB signal 440 received after reflection by the external object 420 may vary according to the external object 420, and a purpose of the electronic device 410. For example, the electronic device 410 may recognize, using the UWB signal 440 received after reflection, whether the external object 420 is a living thing, and when the external object 420 is a person, the electronic device may acquire information regarding a biometric signal and a stress level. As another example, the electronic device 410 may determine a user's motion by using the UWB signal 440 received after reflection, and recognize the user's motion as a gesture to control the electronic device 410.

As described above, UWB signals may be used in UWB ranging, but may also be used as radar signals. Hereinafter, in order to distinguish therebetween, a case where UWB signals are used UWB ranging may be referred to as a UWB ranging mode, and a case where UWB signals are used as radar signals may be referred to as a radar mode. A case where an electronic device uses UWB signals in the UWB ranging mode and the radar mode at the same time is defined as a hybrid mode, and hereinafter, the hybrid mode will be described below.

Figure 5:
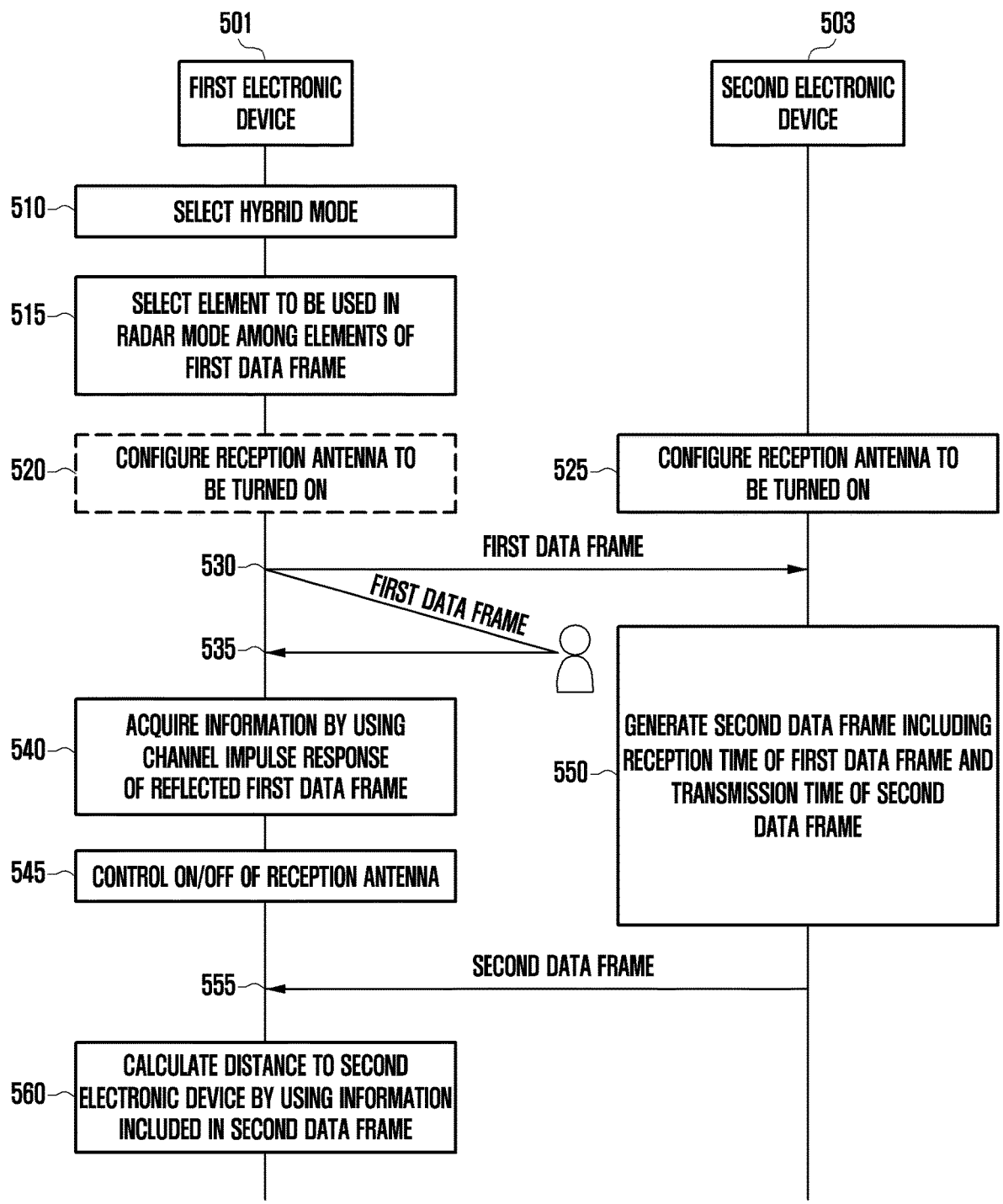
FIG. 5 is a flowchart illustrating a first electronic device using a hybrid mode in a single-side two way ranging method according to an embodiment of the disclosure.

FIG. 5 is a flowchart illustrating a first electronic device using a hybrid mode in a single-side two way ranging method according to an embodiment of the disclosure.

Referring to FIG. 5, according to various embodiments of the disclosure, a first electronic device 501 (e.g., the electronic device 101 in FIG. 1) may select a mode to use a data frame included in a UWB signal based on a current situation (e.g., an application in use). The first electronic device 501 may select one of a UWB ranging mode, a radar mode, and a hybrid mode of using the UWB ranging mode and the radar mode at the same time. The UWB ranging mode may be a mode in which the first electronic device 501 measures a distance to a second electronic device 503 according to the method described with reference to FIG. 2B. The radar mode is a mode in which the first electronic device 501 acquires information according to the method described with reference to FIG. 4. The first electronic device 501 may select the hybrid mode in operation 510. For example, the first electronic device 501 may select the hybrid mode when operating in a sleep mode. As another example, the first electronic device 501 may select the hybrid mode to monitor a health state of a driver while accessing a vehicle.

According to various embodiments of the disclosure, the first electronic device 501 may, in operation 515, select an element to be used in the radar mode among elements of a first data frame (e.g., the data frame 300 in FIG. 3). The first electronic device 501 may select the entirety of the first data frame 300 as elements to be used in the radar mode. Alternatively, the first electronic device 501 may select at least one of a SYNC (e.g., the SYNC 310 in FIG. 3), an SFD (e.g., the SFD 320 in FIG. 3), an STS (e.g., the STS 330 in FIG. 3), a PHR (e.g., the PHR 340 in FIG. 3), and a PHY payload (e.g., the PHY payload 350 in FIG. 3). According to an embodiment of the disclosure, the first electronic device 501 may select the SYNC 310 and/or the STS 330 to acquire sufficient information in the radar mode. According to another embodiment of the disclosure, the first electronic device 501 may also select all elements of the first data frame to acquire sufficient information.

According to various embodiments of the disclosure, the first electronic device 501 may, in operation 520, configure a reception antenna to be turned on. The first electronic device 501 does not know when a reflected signal is received, and thus may configure the reception antenna to be turned on, before transmitting a signal. When the reception antenna is configured to be turned on, the first electronic device 501 may not perform operation 520. According to an embodiment of the disclosure, when an object required to be identified in the radar mode is determined and predictable, the first electronic device 501 may determine in advance a time (e.g., a start time, a maintenance time, and a termination time) for which the reception antenna is configured to be turned on, and configure the reception antenna according to the determined time. For example, when an object required to be identified in the radar mode is predicted to be close, the first electronic device 501 may configure the time for which the reception antenna is configured to be turned on, to be short, and when the object is predicted to be far away, may configure the time for which the reception antenna is configured to be turned on, to be long.

According to various embodiments of the disclosure, the second electronic device 503 may, in operation 525, also configure a reception antenna to be turned on to receive a UWB signal including the first data frame transmitted by the first electronic device 501. The first electronic device 501 and the second electronic device 503 use a single-side two way ranging method, and thus the second electronic device 503 may recognize when the first electronic device 501 transmits an UWB signal. The second electronic device 503 may configure the reception antenna to be turned on, before the first electronic device 501 transmits a UWB signal. Similarly, when the reception antenna is configured to be turned on, the second electronic device 503 may not perform operation 525. According to an embodiment of the disclosure, the first electronic device 501 and the second electronic device 503 may have a prior arrangement about when to transmit or receive a UWB signal, by using a different communication scheme (e.g., Bluetooth communication). According to another embodiment of the disclosure, the first electronic device 501 and the second electronic device 503 may have a prior arrangement about when to transmit or receive a UWB signal, by using a ranging control message.

According to various embodiments of the disclosure, the first electronic device 501 may, in operation 530, transmit a UWB signal including the first data frame. According to an embodiment of the disclosure, the first data frame may be configured to be used in the UWB ranging mode. According to another embodiment of the disclosure, the first electronic device 501 may further configure the SYNC 310 and/or STS 330 previously selected among data frame elements, as a signal to be used in the radar mode so as to generate the first data frame.

According to various embodiments of the disclosure, the first electronic device 501 may, in operation 535, receive a first data frame obtained through reflection of the transmitted first data frame. The first data frame transmitted by the first electronic device 501 may be reflected by a surrounding environment (e.g., building or tree), the second electronic device 503, or a user having the second electronic device 503. The elements of the reflected first data frame may be changed.

According to various embodiments of the disclosure, the first electronic device 501 may, in operation 540, acquire information by using a channel impulse response of the reflected first data frame. The first electronic device 501 may obtain the channel impulse response by using the SYNC 310 and/or STS 330, which are elements selected in operation 515, in the first data frame received after reflection.

Figure 6A:
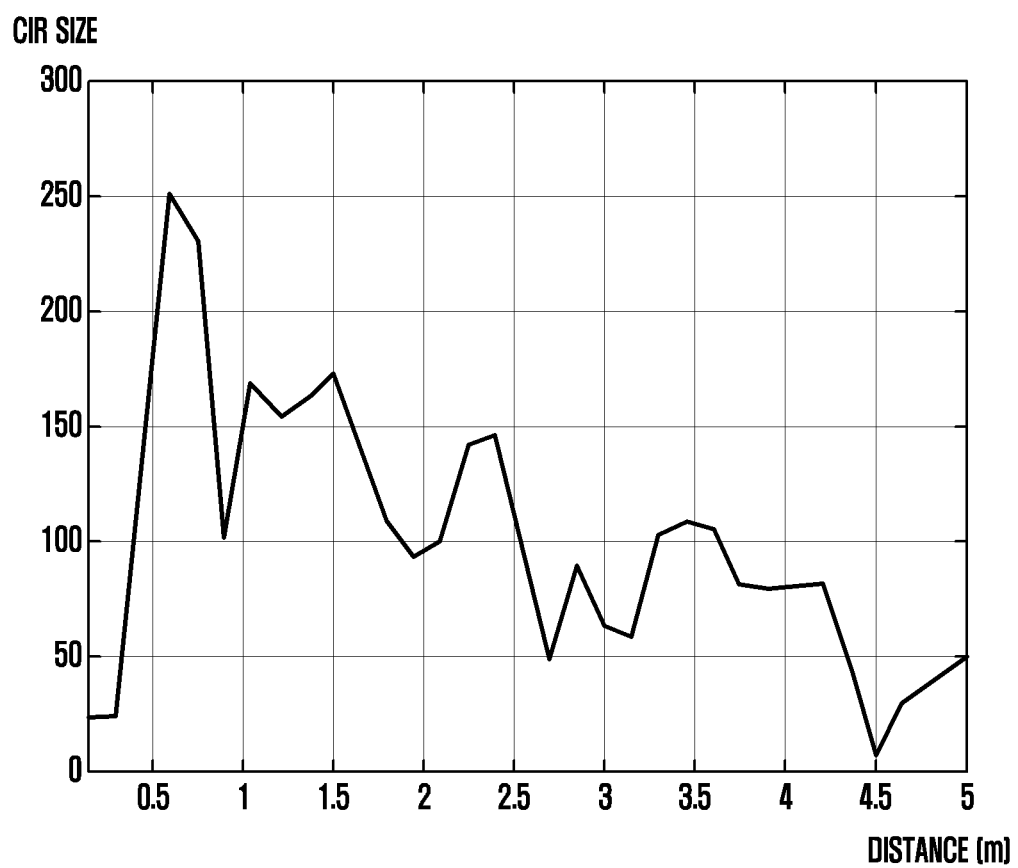
FIG. 6A illustrates a size of a channel impulse response to a distance to a reflector measured in a radar mode by a first electronic device 501 according to an embodiment of the disclosure.

FIG. 6A illustrates a size of a channel impulse response according to a distance to a reflector measured in a radar mode by the first electronic device 501 according to an embodiment of the disclosure. The first electronic device 501 may perform detection of a respiratory rate/heart rate or gesture recognition based on machine learning by removing clutter and/or direct current (DC) from a channel impulse response.

Referring to FIG. 6A, according to various embodiments of the disclosure, the first electronic device 501 may, in operation 545, control ON/OFF of the reception antenna so as to reduce power consumption. When a time to receive a signal reflected at a maximum distance measurable in the radar mode passes, the first electronic device 501 may configure the reception antenna to be turned off so as to reduce power consumption. For example, when the maximum distance measurable in the radar mode by the first electronic device 501 is 9 m, the first electronic device 501 may switch the reception antenna to OFF after 30 ns from the transmission of the first data frame.

Thereafter, since the first electronic device 501 is aware of when the second electronic device 503 transmits a UWB signal including a second data frame, the first electronic device may configure the reception antenna to be turned on again before the second electronic device 503 transmits a UWB signal including the second data frame. According to an embodiment of the disclosure, the first electronic device 501 and the second electronic device 503 may have a prior arrangement about when to transmit or receive a UWB signal, by using a different communication scheme (e.g., Bluetooth communication). According to another embodiment of the disclosure, the first electronic device 501 and the second electronic device 503 may have a prior arrangement about when to transmit or receive a UWB signal, by using a ranging control message.

When the UWB signal including the first data frame transmitted by the first electronic device 501 is received, the second electronic device 503 may, in operation 550, generate a second data frame including a reception time of the first data frame and a transmission time of the second data frame. The reception time of the first data frame and the transmission time of the second data frame may be included in a PHY payload of the second data frame. According to an embodiment of the disclosure, when the transmitted first data frame is received using multiple antennas, the second electronic device 503 may further calculate an angle of arrival (AOA) of the first electronic device 501. The second electronic device 503 may further determine a field of view, based on machine learning.

According to various embodiments of the disclosure, the second electronic device 503 may, in operation 555, transmit the generated second data frame to the first electronic device 501.

According to various embodiments of the disclosure, when a UWB signal including the second data frame is received, the first electronic device 501 may, in operation 560, calculate a distance to the second electronic device 503 by using information included in the second data frame. When the second data frame is received, the first electronic device 501 may calculate a time (time of ply) taken for data to go and return, by using a reception time of the second data frame and times included in the PHY payload of the second data frame, at which the second electronic device 503 has received the first data frame and has transmitted the second data frame. The first electronic device 501 may divide, by 2, the calculated time taken for data to go and return, and multiply the divided time by the velocity of light so as to calculate a distance to the second electronic device 503.

According to an embodiment of the disclosure, when the second data frame is received by multiple antennas, the first electronic device 501 may recognize an angle of arrival of the second electronic device 503, and further determine a field of view, based on machine learning.

Figure 6B:
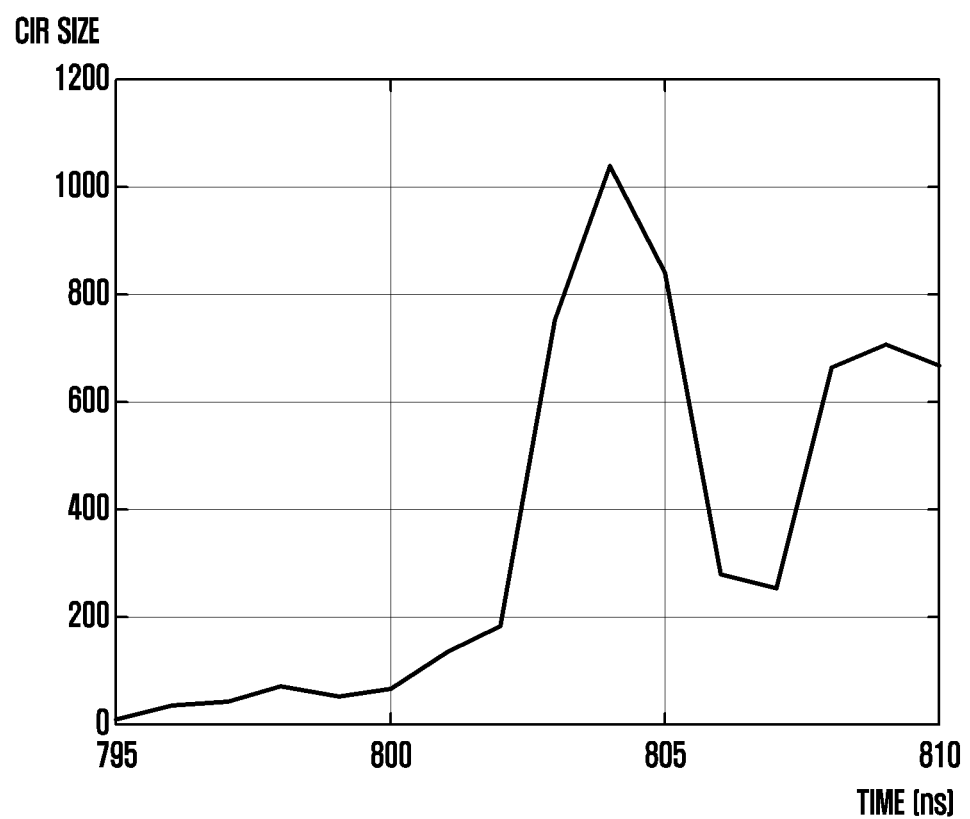
FIG. 6B illustrates a size of a channel impulse response to a distance to a second electronic device measured in a UWB ranging mode by a first electronic device according to an embodiment of the disclosure.

FIG. 6B illustrates a size of a channel impulse response according to a distance to the second electronic device measured in a UWB ranging mode by a first electronic device according to an embodiment of the disclosure.

Referring to FIG. 6B, according to an embodiment of the disclosure, an electronic device may calculate a distance to an external electronic device (e.g., the second electronic device) through application of a signal processing algorithm by using a channel impulse response.

Figure 7:
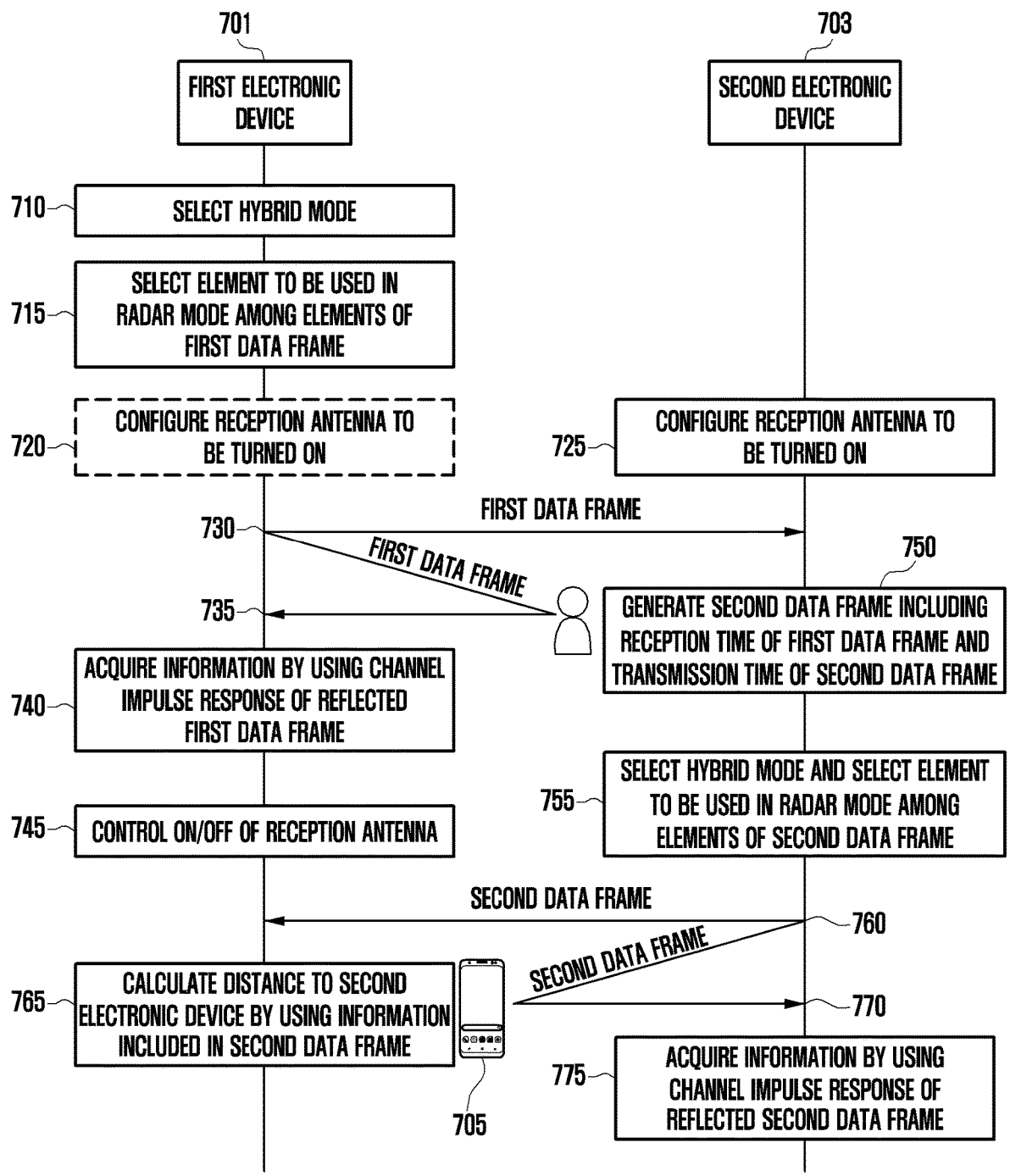
FIG. 7 is a flowchart illustrating a first electronic device and a second electronic device using a hybrid mode in a SS-TWR scheme according to an embodiment of the disclosure.

FIG. 7 is a flowchart illustrating a first electronic device and a second electronic device using a hybrid mode in an SS-TWR scheme according to an embodiment of the disclosure.

Referring to FIG. 7, the example in which a first electronic device and a second electronic device use the hybrid mode in the SS-TWR scheme as described with reference to FIG. 7 is similar to an example in which the first electronic device uses the hybrid mode in the SS-TWR scheme as described with reference to FIG. 5. Therefore, a detailed description of the same/similar operations may be omitted in FIG. 7.

According to various embodiments of the disclosure, a first electronic device 701 (e.g., the electronic device 101 in FIG. 1) may select one of a UWB ranging mode, a radar mode, and a hybrid mode of using the UWB ranging mode and the radar mode at the same time based on a current situation (e.g., an application in use). The first electronic device 701 may select the hybrid mode in operation 710. For example, while the first electronic device 701 is moving, the first electronic device may select the hybrid mode and determine whether an obstacle appear between a second electronic device 703 and the first electronic device. As another example, in a case where the first electronic device 701 is a smart watch, and the second electronic device 703 is a mobile phone, when the second electronic device 703 is discovered, the first electronic device 701 may operate in the radar mode or the hybrid mode to further measure a user's heart rate while operating in the UWB ranging mode for the second electronic device 703. When the second electronic device 703 is not discovered, the first electronic device 701 may operate in the radar mode to measure the user's heart rate. As another example, when the vehicle 703 is discovered as the second electronic device 703, the first electronic device 701 may measure a distance to the vehicle in the UWB ranging mode so as to determine whether the first electronic device 701 is in the vehicle 703, and monitor a driver's health state (e.g., heart rate or respiratory rate) in the radar mode.

According to various embodiments of the disclosure, the first electronic device 701 may, in operation 715, select an element to be used in the radar mode among elements of a first data frame (e.g., the data frame 300 in FIG. 3). The first electronic device 701 may select the SYNC 310 and/or the STS 330 among a SYNC (e.g., the SYNC 310 in FIG. 3), an SFD (e.g., the SFD 320 in FIG. 3), an STS (e.g., the STS 330 in FIG. 3), a PHR (e.g., the PHR 340 in FIG. 3), and a PHY payload (e.g., the PHY payload 350 in FIG. 3) so as to acquire sufficient information in the radar mode.

According to various embodiments of the disclosure, in operation 720, since the first electronic device 701 does not know when a reflected signal is received, the first electronic device may configure a reception antenna to be turned on, before transmitting a signal. According to an embodiment of the disclosure, when the first electronic device 701 is aware of when a reflected signal is received, the first electronic device may control ON/OFF of the reception antenna, based on the reception time.

According to various embodiments of the disclosure, the second electronic device 703 may, in operation 725, configure a reception antenna to be turned on to receive the first data frame transmitted by the first electronic device 701. The second electronic device 703 is aware of when the first electronic device 701 transmits the first data frame, and thus may configure the reception antenna to be turned on, before the first electronic device 701 transmits the first data frame.

According to various embodiments of the disclosure, the first electronic device 701 may, in operation 730, transmit the first data frame. The first electronic device 701 may configure the SYNC 310 and/or STS 330 previously selected among data frame elements, as a signal to be used in the radar mode so as to generate and transmit the first data frame.

According to various embodiments of the disclosure, the first electronic device 701 may, in operation 735, receive a first data frame obtained through reflection of the transmitted first data frame. The first data frame may collide with, for example, a user of the second electronic device 703 and then be reflected thereby.

According to various embodiments of the disclosure, the first electronic device 701 may, in operation 740, acquire information by using a channel impulse response of the reflected first data frame. The first electronic device 701 may, from the channel impulse response, detect a respiratory rate/heart rate or acquire information, such as a gesture based on machine learning.

According to various embodiments of the disclosure, the first electronic device 701 may, in operation 745, control ON/OFF of the reception antenna so as to reduce power consumption. When a time to receive a signal reflected at a maximum distance measurable in the radar mode passes, the first electronic device 701 may configure the reception antenna to be turned off. Thereafter, since the first electronic device 701 is aware of when the second electronic device 703 transmits a second data frame, the first electronic device may configure the reception antenna to be turned on, before the second electronic device 703 transmits the second data frame.

According to various embodiments of the disclosure, when the first data frame transmitted by the first electronic device 701 is received, the second electronic device 703 may, in operation 750, generate the second data frame including a reception time of the first data frame and a transmission time of the second data frame. The reception time of the first data frame and the transmission time of the second data frame may be included in a PHY payload of the second data frame. According to an embodiment of the disclosure, when the transmitted first data frame is received using multiple antennas, the second electronic device 703 may further calculate an AOA of the first electronic device 701. The second electronic device 703 may further determine a field of view, based on machine learning.

According to various embodiments of the disclosure, the second electronic device 703 may, in operation 755, select the hybrid mode among the UWB ranging mode, the radar mode, and the hybrid mode of using the UWB ranging mode and the radar mode at the same time based on a current situation (e.g., a situation of linking with the first electronic device 701). The second electronic device 703 may select the SYNC 310 and/or the STS 330 to be used in the radar mode among elements of the second data frame, but the disclosure is not limited thereto.

According to various embodiments of the disclosure, the second electronic device 703 may, in operation 760, transmit the second data frame. The second electronic device 703 may configure the SYNC 310 and/or STS 330 previously selected among data frame elements, as a signal to be used in the radar mode so as to generate and transmit the second data frame. The second electronic device 703 may identify whether the reception antenna is configured to be turned on, before transmitting the second data frame, and when the reception antenna is not ON, may change the configuration of the reception antenna to be turned on.

According to various embodiments of the disclosure, when the second data frame is received, the first electronic device 701 may, in operation 765, calculate a distance to the second electronic device 703 by using information included in the second data frame. When the second data frame is received, the first electronic device 701 may calculate a time taken for data to go and return, by using a reception time of the second data frame and times included in the PHY payload of the second data frame, at which the second electronic device 703 has received the first data frame and has transmitted the second data frame. The first electronic device 701 may divide, by 2, the calculated time taken for data to go and return, and multiply the divided time by the velocity of light so as to calculate a distance to the second electronic device 703.

According to an embodiment of the disclosure, when the second data frame is received by multiple antennas, the first electronic device 701 may recognize an angle of arrival of the second electronic device 703, and further determine a field of view, based on machine learning.

According to various embodiments of the disclosure, the second electronic device 703 may, in operation 770, receive a second data frame obtained through reflection of the transmitted second data frame. The second data frame may collide with and then be reflected by, for example, an external electronic device 705, whereby the second electronic device 703 receives the second data frame. As another example, the second data frame may also collide with and then be reflected by the first electronic device 701, whereby the second electronic device 703 receives the second data frame.

According to various embodiments of the disclosure, the second electronic device 703 may, in operation 775, acquire information by using a channel impulse response of the second data frame received after reflection.

According to various embodiments of the disclosure, the first electronic device 701 may measure a distance in the UWB ranging mode with the second electronic device 703 operating as an anchor, and recognize the location of the second electronic device 703, thereby operating as a navigation in a house or a public space. At the same time, the first electronic device 701 may recognize a user's gesture in the radar mode.

Figure 8:
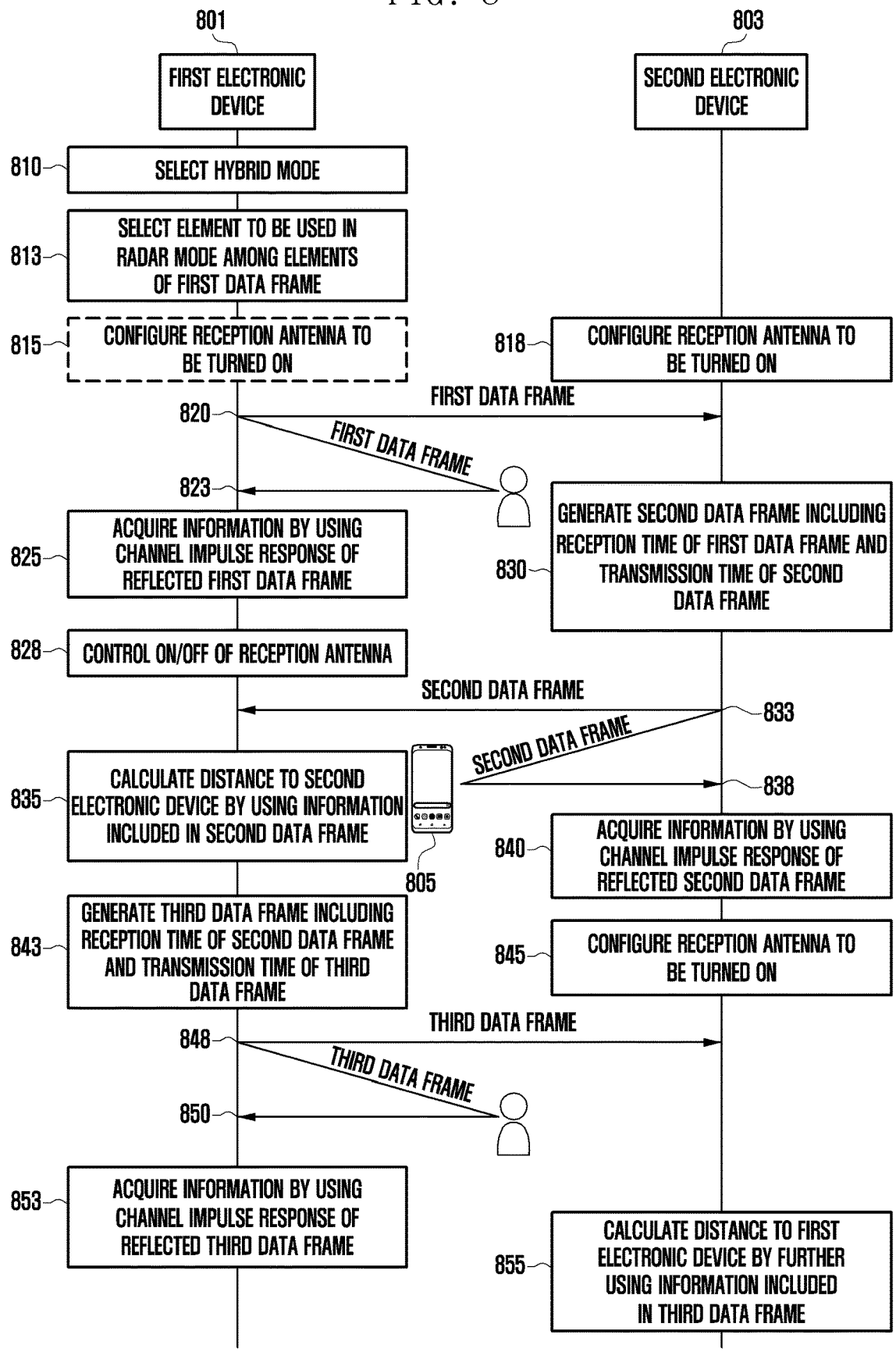
FIG. 8 is a flowchart illustrating a first electronic device using a hybrid mode in a double-side two way ranging method (DS-TWR) scheme according to an embodiment of the disclosure.

FIG. 8 is a flowchart illustrating a first electronic device using a hybrid mode in a DS-TWR scheme according to an embodiment of the disclosure.

Referring to FIG. 8, according to various embodiments of the disclosure, a first electronic device 801 (e.g., the electronic device 501 in FIG. 5) may select one of a UWB ranging mode, a radar mode, and a hybrid mode of using the UWB ranging mode and the radar mode at the same time based on a current situation (e.g., an application in use). The UWB ranging mode may be a mode in which the first electronic device 801 measures a distance to a second electronic device 803 (e.g., the second electronic device 503 in FIG. 5) according to the method described with reference to FIG. 2C. The radar mode is a mode in which the first electronic device 801 acquires information according to the method described with reference to FIG. 4. The first electronic device 801 may select the hybrid mode in operation 810.

The example in which a first electronic device uses the hybrid mode in the DS-TWR scheme as described with reference to FIG. 8 is similar to an example in which the first electronic device uses the hybrid mode in the SS-TWR scheme as described with reference to FIG. 5.

According to various embodiments of the disclosure, operation 813 to operation 830 in FIG. 8 may correspond to operation 515 to operation 550 in FIG. 5, and thus may be omitted here to avoid overlapping of description. According to various embodiments of the disclosure, operation 833 to operation 840 in FIG. 8 may correspond to operation 760 to operation 775 in FIG. 7, and thus may be omitted here to avoid overlapping of description.

According to various embodiments of the disclosure, when a second data frame transmitted by the second electronic device 803 is received, the first electronic device 801 may, in operation 843, generate a third data frame including a reception time of the second data frame and a transmission time of the third data frame. The reception time of the second data frame and the transmission time of the third data frame may be included in a PHY payload of the third data frame.

According to various embodiments of the disclosure, the second electronic device 803 may, in operation 845, configure a reception antenna to be turned on to receive the third data frame.

According to various embodiments of the disclosure, the first electronic device 801 may, in operation 848, transmit the third data frame. The first electronic device 801 may configure the SYNC 310 and STS 330 previously selected among data frame elements in operation 813, as a signal to be used in the radar mode so as to generate and transmit the third data frame. According to an embodiment of the disclosure, the SYNC 310 and STS 330 of the third data frame may be different from the SYNC 310 and STS 330 of the first data frame.

According to various embodiments of the disclosure, the first electronic device 801 may, in operation 850, receive a third data frame obtained through reflection of the transmitted third data frame. The third data frame transmitted by the first electronic device 801 may be reflected by a surrounding environment (e.g., building or tree), the second electronic device 803, or a user having the second electronic device 803. A reflector of the third data frame may be the same as that of the first data frame.

According to various embodiments of the disclosure, the first electronic device 801 may, in operation 853, acquire information by using a channel impulse response of the reflected third data frame. The first electronic device 801 may obtain the channel impulse response by using the SYNC 310 and STS 330, which are elements selected in operation 813, in the third data frame received after reflection. The first electronic device 801 may perform detection of a respiratory rate/heart rate or gesture recognition based on machine learning by further considering the channel impulse response obtained in operation 825.

According to various embodiments of the disclosure, when the third data frame is received, the second electronic device 803 may, in operation 855, calculate a distance to the first electronic device 801 by using information included in the third data frame. When the third data frame is received, the second electronic device 703 may calculate a time taken for data to go and return, by using a reception time of the third data frame and times included in the PHY payload of the third data frame, at which the second electronic device 703 has received the second data frame and has transmitted the third data frame. The second electronic device 703 may divide, by 2, the calculated time taken for data to go and return, and multiply the divided time by the velocity of light so as to calculate a distance to the first electronic device 701.

Figure 9A:
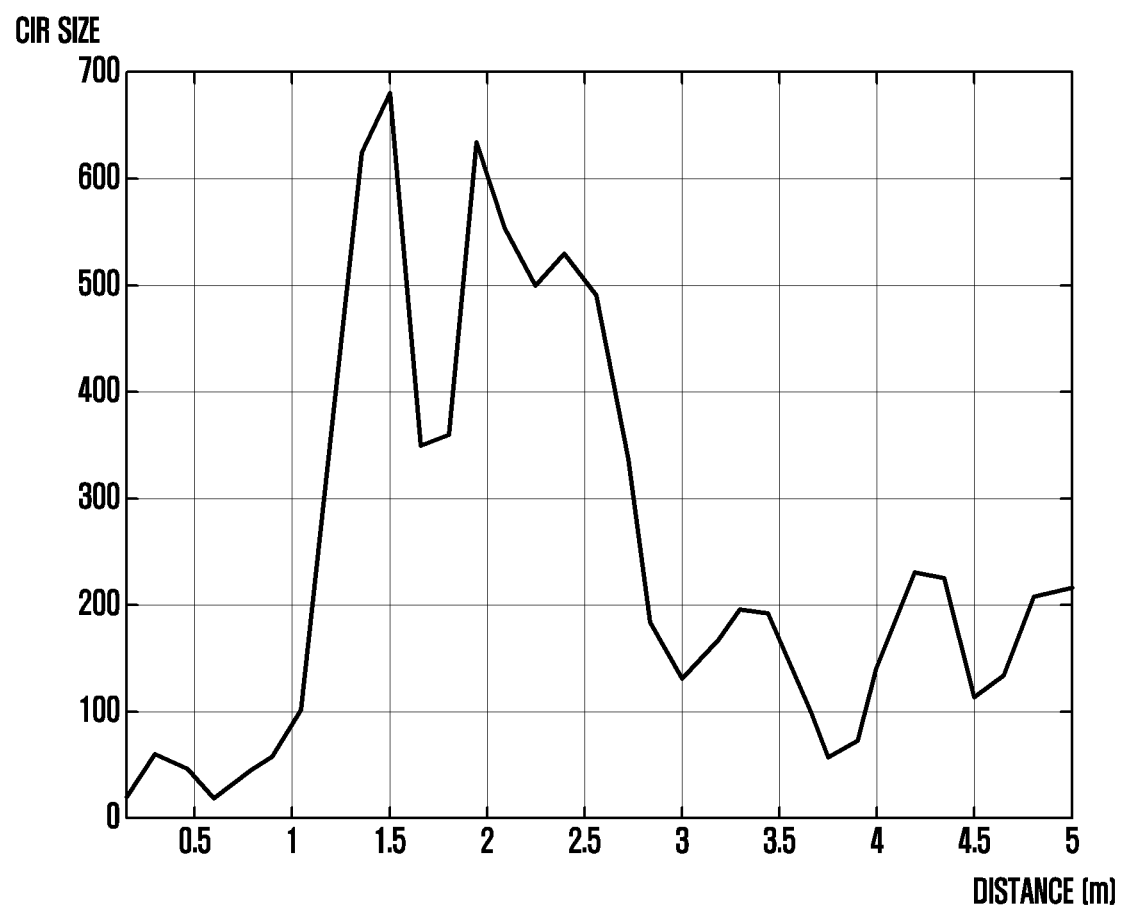
FIGS. 9A, 9B, and 9C are diagrams illustrating channel impulse responses obtained in FIG. 8 according to various embodiments of the disclosure.
Figure 9B:
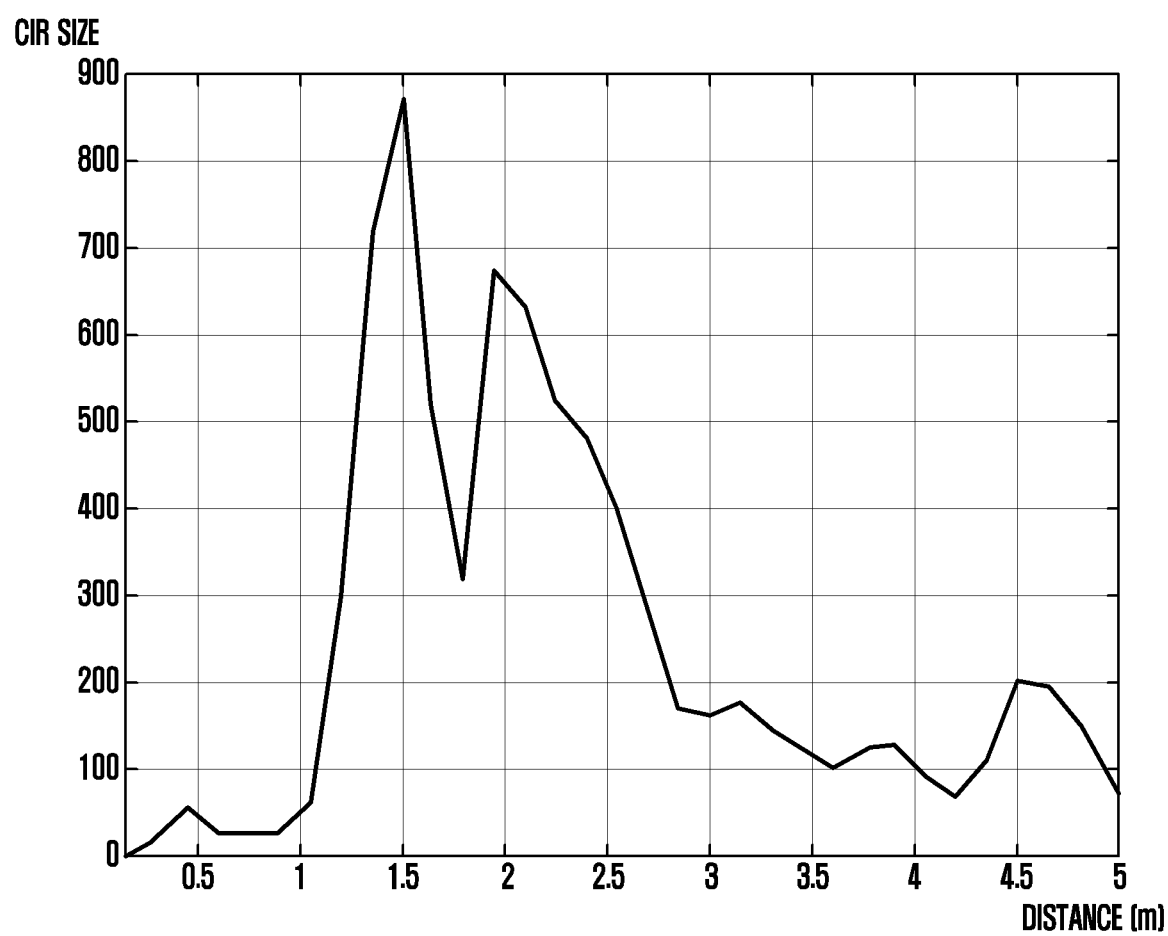
Figure 9C:
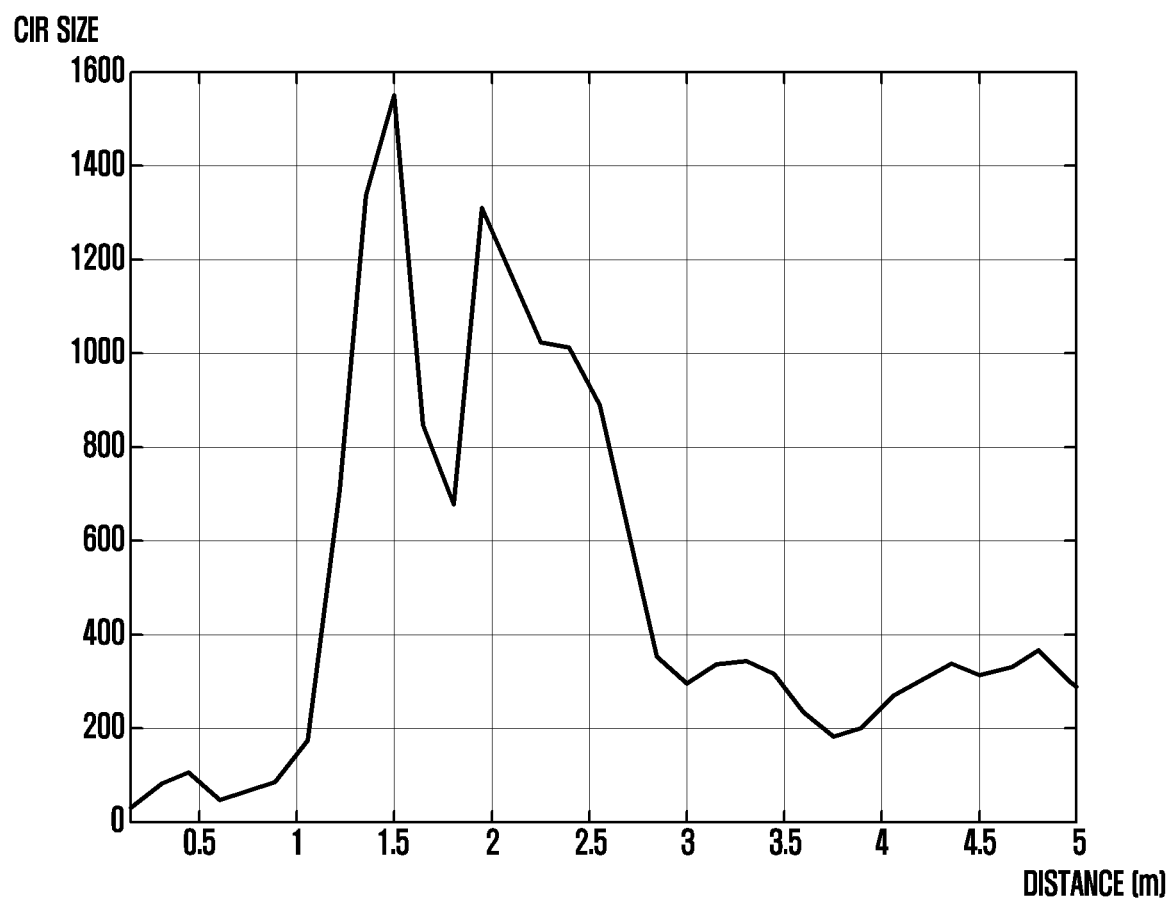

According to various embodiments of the disclosure, an electronic device may use multiple channel impulse responses in order to improve a signal-to-noise ratio (SNR) in the radar mode. FIGS. 9A to 9C may be diagrams for the following description on whether an SNR and is improved when multiple channel impulse responses are used.

FIGS. 9A, 9B, and 9C illustrate channel impulse responses obtained in FIG. 8 according to various embodiments of the disclosure.

Referring to FIG. 8, the first electronic device 801 have obtained the channel impulse response of the reflected first data frame in operation 825, and have obtained the channel impulse response of the reflected third data frame in operation 853.

Referring to FIG. 9A, it illustrates the channel impulse response of the reflected first data frame, which is obtained by the first electronic device 801 in operation 825.

Referring to FIG. 9B, it illustrates the channel impulse response of the reflected first data frame, which is obtained by the first electronic device 801 in operation 880.

Referring to FIG. 9C, it illustrates a channel impulse response which is the sum of FIGS. 9A and 9B.

In comparison between FIGS. 9C and 9A and 9B, it may be noted that the size of the channel impulse response in FIG. 9C has a large peak value. When the peak of the size of a channel impulse response gets large, an SNR thereof may be improved.

Figure 10A:
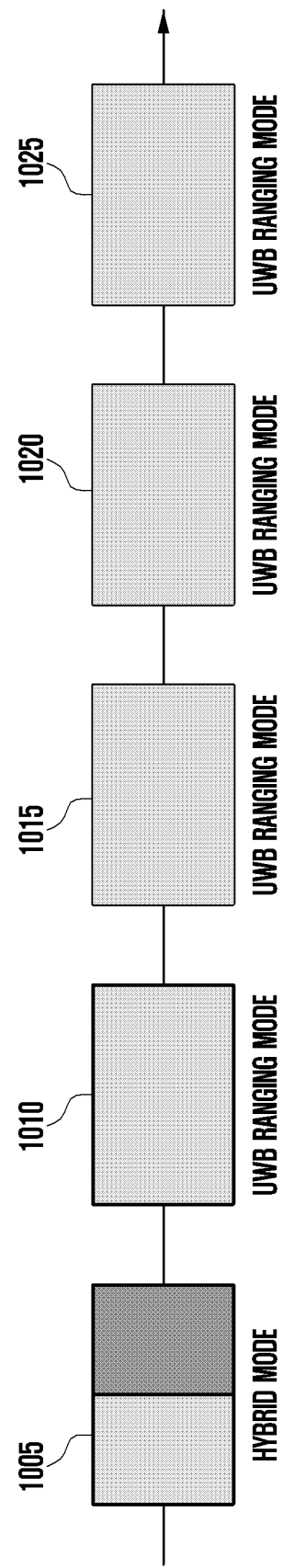
FIGS. 10A and 10B are diagrams illustrating using a data frame in various modes according to various embodiments of the disclosure.
Figure 10B:
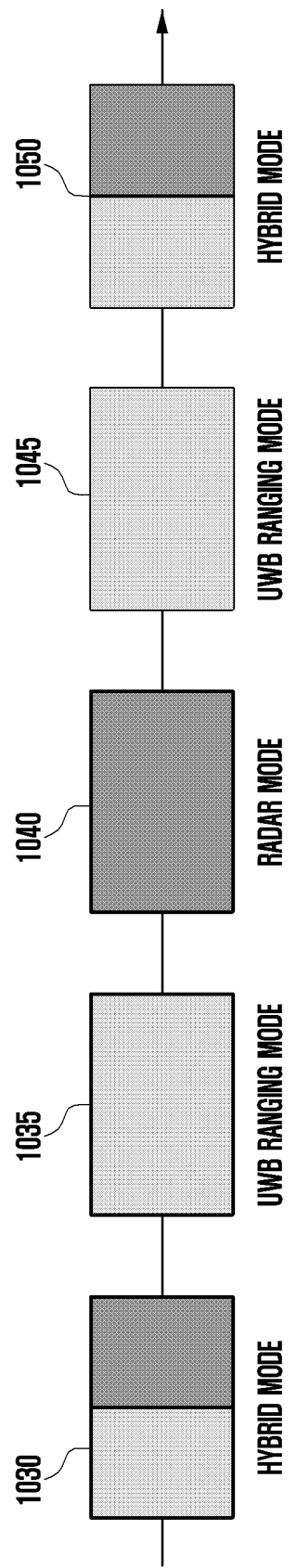

FIGS. 10A and 10B are diagrams illustrating using a data frame in various modes according to various embodiments of the disclosure.

Referring to FIG. 10A, it illustrates an example in which an electronic device occasionally uses the radar mode together while consistently using the UWB ranging mode. For example, when a problem occurs in communication while an electronic device uses the UWB ranging mode with another electronic device, the electronic device may further determine, in the radar mode, whether there is an obstacle, so as to determine whether there is an obstacle between the electronic device and the other electronic device. In a case where, while using the UWB ranging mode with another electronic device, the electronic device is required to use the UWB ranging mode and the radar mode together in order to further determine whether there is an obstacle, the electronic device may configure a hybrid mode 1005, and in other cases, the electronic device may configure and use UWB ranging modes 1010, 1015, 1020, and 1025. According to an embodiment of the disclosure, the electronic device may periodically transmit a data frame configured for the hybrid mode 1005.

Referring to FIG. 10B, the electronic device may selectively use the UWB ranging mode, the radar mode, and the hybrid mode. The electronic device may select and use one of the UWB ranging mode, the radar mode, and the hybrid mode based on a current situation. For example, in a case where the electronic device (or another electronic device) is moving, the electronic device may periodically use the radar mode in order to further determine whether there is an obstacle while the electronic device is moving. Even when there is no need to use the UWB ranging mode, the electronic device may use only the radar mode in order to determine whether there is an obstacle. FIG. 10B may illustrate an example in which an electronic device uses a hybrid mode 1030 first, then uses a UWB ranging mode 1035 and a radar mode 1040, and uses again a UWB ranging mode 1045 and a hybrid mode 1050 in that order. According to an embodiment of the disclosure, the electronic device may transmit data frames configured for the UWB ranging mode 1035, the radar mode 1040, and the hybrid mode 1005 in a designated pattern.

Figure 11:
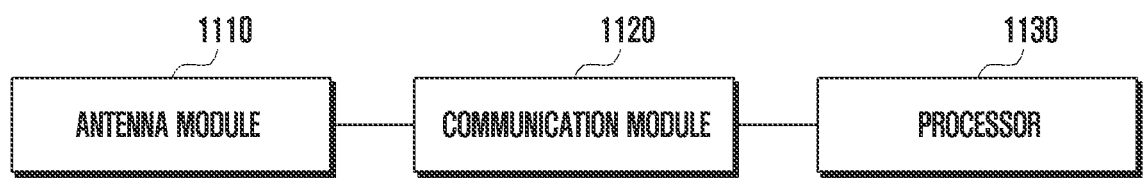
FIG. 11 is a block diagram illustrating a configuration of an electronic device according to an embodiment of the disclosure.

FIG. 11 is a block diagram illustrating a configuration of an electronic device according to an embodiment of the disclosure.

Referring to FIG. 11, an electronic device (e.g., the first electronic device 501 in FIG. 5) may include an antenna module 1110 (e.g., the antenna module 197 in FIG. 1), a communication module 1120 (e.g., the communication module 190 in FIG. 1), and a processor 1130 (e.g., the processor 120 in FIG. 1).

According to various embodiments of the disclosure, the antenna module 1110 may include at least one antenna. For example, the antenna module 1110 may include multiple reception antennas and one transceiving antenna. The one transceiving antenna may operate in a transmission mode or a reception mode. When a signal is received by the multiple reception antennas, the processor 1130 may further recognize an azimuth of the received signal. According to an embodiment of the disclosure, the antenna module 1110 may be configured to be turned on or OFF by a control of the communication module 1120.

According to various embodiments of the disclosure, the communication module 1120 may be a UWB communication module. The communication module 1120 may receive a signal from the processor 1130 so as to control the antenna module 1110. According to an embodiment of the disclosure, the communication module 1120 may select some of the multiple antennas included in the antenna module 1110. For example, when the antenna module 1110 includes multiple reception antennas, the communication module 1120 may select some of the multiple reception antennas based on the positions of the reception antennas. The communication module 1120 may configure a reception antenna to be turned on, before signal reception, and when there is no signal to receive, may configure the reception antenna to be turned off so as to reduce power consumption.

According to various embodiments of the disclosure, the processor 1130 may control the communication module 1120 to perform various embodiments described in the disclosure. Specifically, the processor 1130 may determine a mode to use UWB signals based on a current situation. The processor 1130 may select one of the UWB ranging mode, the radar mode, or the hybrid mode and use UWB signals.

According to various embodiments of the disclosure, the processor 1130 may receive a UWB signal transmitted by an external electronic device, and calculate a distance to the external electronic device and/or an azimuth thereof. The processor 1130 may perform communication with the external electronic device by using UWB signals.

According to various embodiments of the disclosure, the processor 1130 may acquire information by using a signal received after reflection. For example, the processor 1130 may use a signal received after reflection to determine whether a reflector is a living thing, and determine a biometric signal or a stress level if the reflector is a person, and may use signals consecutively received after reflection to determine a movement of the reflector.

Figure 12:
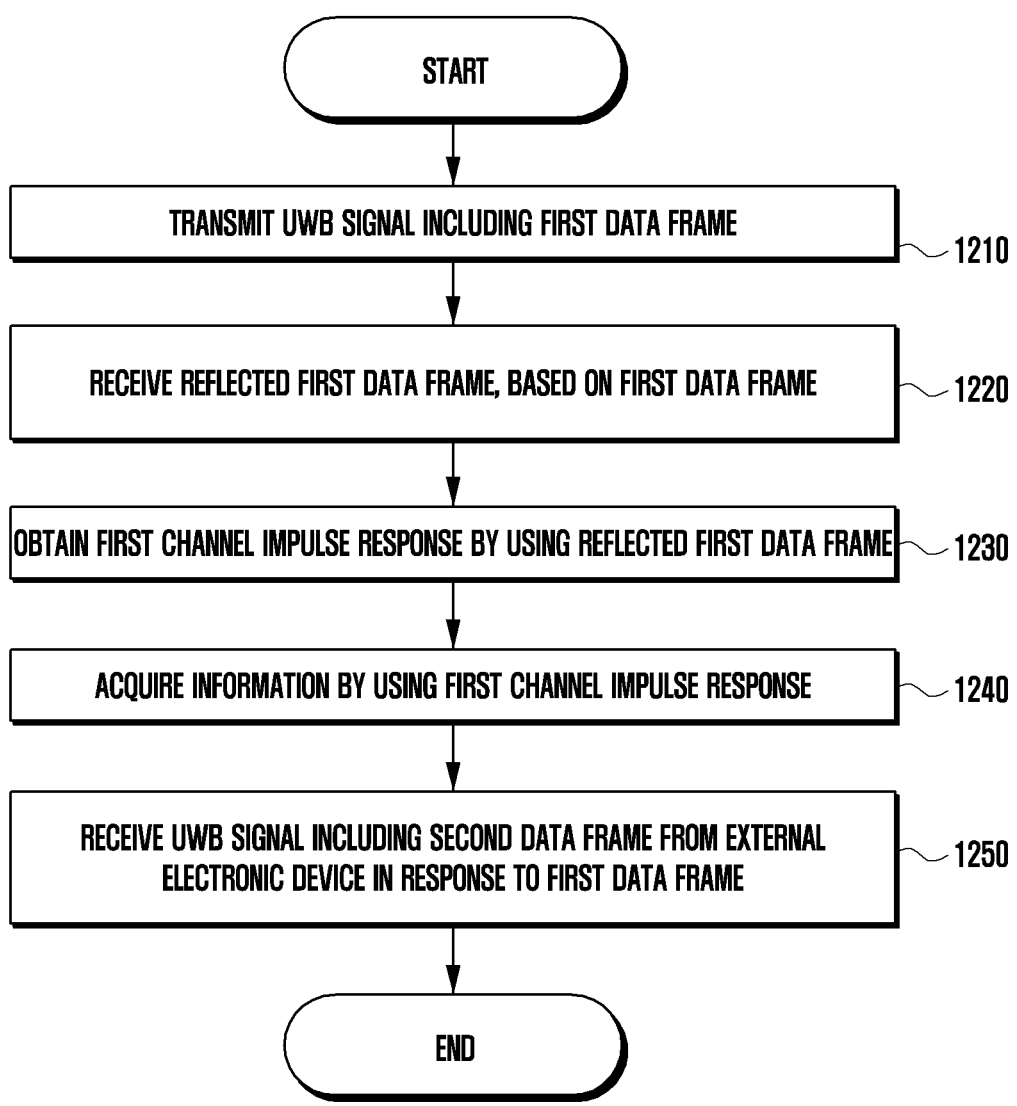
FIG. 12 is a flowchart of an electronic device according to an embodiment of the disclosure.

FIG. 12 is a flowchart of an electronic device according to an embodiment of the disclosure.

Referring to FIG. 12, according to various embodiments of the disclosure, an electronic device (e.g., the electronic device 501 in FIG. 5) may be a device which is intended to measure a distance to an external electronic device (e.g., the second electronic device 503 in FIG. 5) through communication by using UWB signals, and also use the UWB signals as radar signals at the same time.

According to various embodiments of the disclosure, the electronic device 501 may, in operation 1210, transmit a UWB signal including a first data frame (e.g., the data frame 300 in FIG. 3). The electronic device 501 may transmit the UWB signal in order to perform UWB communication with the external electronic device 503. For example, the electronic device 501 may transmit the first data frame 300 including a transmission time of the first data frame to the external electronic device 503.

According to various embodiments of the disclosure, the electronic device 501 may, in operation 1220, receive a reflected first data frame, based on the first data frame 300. When the first data frame 300 configured in a pulse type is reflected, the pulse configuration thereof may be changed.

According to various embodiments of the disclosure, the electronic device 501 may, in operation 1230, obtain a first channel impulse response by using the reflected first data frame. The electronic device 501 may obtain the first channel impulse response in order to obtain a distance to the external electronic device 503 with which the first data frame collides.

According to various embodiments of the disclosure, the electronic device 501 may, in operation 1240, acquire information by using the first channel impulse response. The electronic device 501 may apply the first channel impulse response to a signal processing algorithm to obtain a distance to the external electronic device 503.

According to various embodiments of the disclosure, the electronic device 501 may, in operation 1250, receive a UWB signal including a second data frame from the external electronic device 503 in response to the first data frame. For example, the external electronic device 503 may transmit a UWB signal including the second data frame including a reception time of first data and a time to transmit second data.

Figure 13:
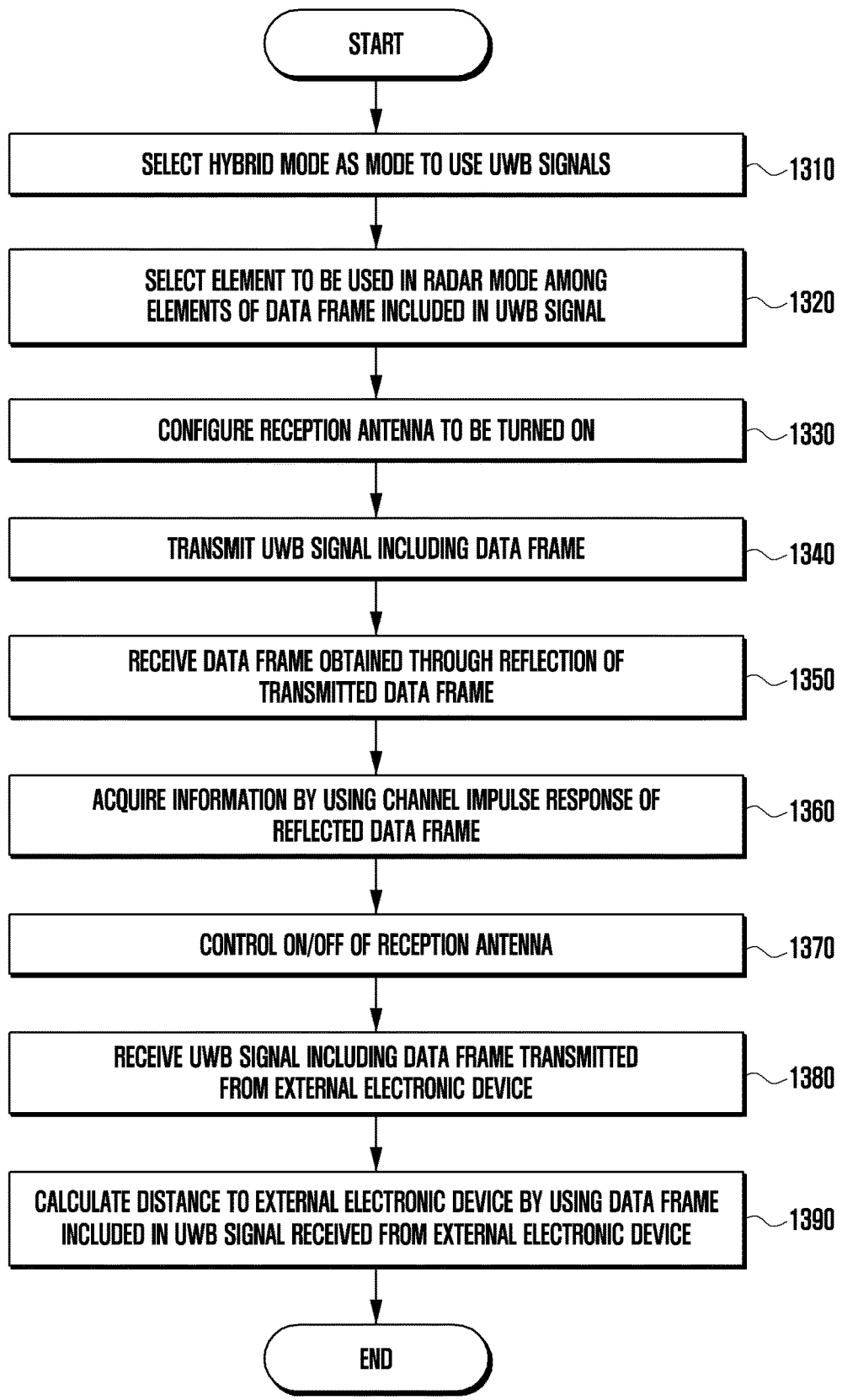
FIG. 13 is a flowchart of an electronic device according to an embodiment of the disclosure.

FIG. 13 is a flowchart of an electronic device according to an embodiment of the disclosure.

Referring to FIG. 13, according to various embodiments of the disclosure, an electronic device (e.g., the electronic device 501 in FIG. 5) may be a device which is intended to measure a distance to an external electronic device through communication by using UWB signals, and also use the UWB signals as radar signals at the same time.

According to various embodiments of the disclosure, the electronic device 501 may, in operation 1310, select a hybrid mode as a mode to use UWB signals. The hybrid mode may be a mode of using UWB signals in a UWB ranging mode and a radar mode at the same time.

According to various embodiments of the disclosure, the electronic device 501 may, in operation 1320, select an element to be used in the radar mode among elements of a data frame (e.g., the data frame 300 in FIG. 3) included in a UWB signal. The electronic device 501 may select the entirety of the data frame as elements to be used in the radar mode, or may select at least one element. According to an embodiment of the disclosure, the electronic device 501 may select a SYNC (e.g., the SYNC 310 in FIG. 3) and an STS (e.g., the STS 330 in FIG. 3) among data frame elements.

According to various embodiments of the disclosure, the electronic device 501 may, in operation 1330, configure a reception antenna to be turned on. The electronic device 501 does not know when a reflected signal is received, and thus may configure the reception antenna to be turned on, before transmitting a signal.

According to various embodiments of the disclosure, the first electronic device 501 may, in operation 1340, transmit the UWB signal including the data frame. For example, the electronic device 501 may transmit the data frame including a transmission time of the data frame in order to measure a distance to the external electronic device. The data frame transmitted by the electronic device 501 may be configured in a pulse type.

According to various embodiments of the disclosure, the electronic device 501 may, in operation 1350, receive a data frame obtained through reflection of the transmitted data frame. The data frame transmitted by the electronic device 501 may collide with and then be reflected by an external object, and the reflected data frame may be received by the electronic device 501. The pulse configuration of the reflected data frame may be different from that of the transmitted data frame. The pulse configuration of the reflected data frame may vary according to at least one of a distance to the external object, and a movement speed of the external object if it is moving.

According to various embodiments of the disclosure, the electronic device 501 may, in operation 1360, acquire information by using a channel impulse response of the reflected data frame. The electronic device 501 may obtain the channel impulse response by using a selected element among the elements of the data frame received after reflection. The electronic device 501 may apply the channel impulse response to a signal processing algorithm. The electronic device 501 may calculate a distance to the external object through the signal processing algorithm.

According to various embodiments of the disclosure, the electronic device 501 may, in operation 1370, control ON/OFF of the reception antenna. When a time to receive a signal reflected at a maximum distance measurable in the radar mode passes, the electronic device 501 may configure the reception antenna to be turned off, and then before receiving a UWB signal from the external electronic device 503, may configure the reception antenna to be turned on. The electronic device 501 may control the configuration of the reception antenna so as to reduce power consumption. According to another embodiment of the disclosure, the electronic device 501 may maintain the configuration of the reception antenna to be turned on, and receive a signal.

According to various embodiments of the disclosure, the electronic device 501 may, in operation 1380, receive a UWB signal including a data frame transmitted from the external electronic device 503. The electronic device 501 may receive the UWB signal by using at least one antenna. For example, the data frame transmitted from the external electronic device 503 may include times at which the external electronic device 503 has received the data frame (e.g., a first data frame) and is to transmit the data frame (e.g., a second data frame).

According to various embodiments of the disclosure, the electronic device 501 may, in operation 1390, calculate a distance to the external electronic device 503 by using the data frame included in the UWB signal received from the external electronic device 503. When the UWB signal is received by multiple antennas, the electronic device 501 may recognize an AOA of the external electronic device 503, and thus further determine a field of view.

An electronic device according to various embodiments of the disclosure may include the antenna module 1110, the communication module 1120 configured to control the antenna module, and the processor 1130 operatively connected to the communication module, wherein the processor 1130 transmits a ultra-wide band (UWB) signal including the first data frame 300, receives, based on the transmitted first data frame, a reflected first data frame, obtains a first channel impulse response by using the reflected first data frame, acquires information by using the channel impulse response, and receives a UWB signal including a second data frame from an external electronic device in response to the transmitted first data frame.

The processor 1130 of the electronic device according to various embodiments of the disclosure may configure a reception antenna of the antenna module 1110 to be turned on, before transmitting the first data frame.

The processor 1130 of the electronic device according to various embodiments of the disclosure may configure the reception antenna to be turned off, when a maximum allowable time for which the transmitted first data frame is reflected and then received has passed.

The processor 1130 of the electronic device according to various embodiments of the disclosure may determine to use the UWB signal including the first data frame in a UWB ranging mode and a radar mode at the same time, before transmitting the first data frame.

The processor 1130 of the electronic device according to various embodiments of the disclosure may further select an element to be used in the radar mode among elements of the first data frame.

In the electronic device according to various embodiments of the disclosure, the selected element may correspond to the SYNC 310 and the scrambled time stamp secure (STS) 330.

The processor 1130 of the electronic device according to various embodiments of the disclosure may transmit a UWB signal including a third data frame to the external electronic device in response to the second data frame, receive, based on the transmitted third data frame, a reflected third data frame, obtain a second channel impulse response by using the reflected third data frame, and further acquire information, based on the first channel impulse response and the second channel impulse response.

In the electronic device according to various embodiments of the disclosure, the information acquirable using the first channel impulse response may correspond to one of existence or absence of a living thing, a heart rate, and a movement of an object.

In the electronic device according to various embodiments of the disclosure, the second data frame may include information on a time at which the external electronic device has received the first data frame and a time at which the external electronic device transmits the second data frame, and the processor 1130 may calculate a distance to the external electronic device by using a transmission time of the first data frame and the information included in the second data frame.

In the electronic device according to various embodiments of the disclosure, the antenna module 1110 may include multiple antennas, and the processor 1130 may receive the UWB signal including the second data frame by using the multiple antennas, and further identify direction information of the external electronic device by using information on a time at which the UWB signal including the second data frame is received using the multiple antennas.

A method of operating an electronic device according to various embodiments of the disclosure may include transmitting a ultra-wide band (UWB) signal including the first data frame 300 (operation 1210), receiving, based on the transmitted first data frame, a reflected first data frame (operation 1220), obtaining a first channel impulse response by using the reflected first data frame (operation 1230), acquiring information by using the channel impulse response (operation 1240), and receiving a UWB signal including a second data frame from an external electronic device in response to the transmitted first data frame (operation 1250).

The method of operating the electronic device according to various embodiments of the disclosure may further include configuring a reception antenna to be turned on, before transmitting the first data frame.

The method of operating the electronic device according to various embodiments of the disclosure may further include configuring the reception antenna to be turned off, when a maximum allowable time for which the transmitted first data frame is reflected and then received has passed.

The method of operating the electronic device according to various embodiments of the disclosure may further include determining to use the UWB signal including the first data frame in a UWB ranging mode and a radar mode at the same time, before transmitting the first data frame.

The method of operating the electronic device according to various embodiments of the disclosure may further include selecting an element to be used in the radar mode among elements of the first data frame.

In the method of operating the electronic device according to various embodiments of the disclosure, the selected element may correspond to the SYNC 310 and the scrambled timestamp secure (STS) 330.

The method of operating the electronic device according to various embodiments of the disclosure may further include transmitting a UWB signal including a third data frame to the external electronic device in response to the second data frame, receiving, based on the transmitted third data frame, a reflected third data frame, obtaining a second channel impulse response by using the reflected third data frame, and acquiring information, based on the first channel impulse response and the second channel impulse response.

In the method of operating the electronic device according to various embodiments of the disclosure, the information acquirable using the first channel impulse response may correspond to one of existence or absence of a living thing, a heart rate, and a movement of an object.

In the method of operating the electronic device according to various embodiments of the disclosure, the second data frame may include information on a time at which the external electronic device has received the first data frame and a time at which the external electronic device transmits the second data frame, and the method may further include calculating a distance to the external electronic device by using a transmission time of the first data frame and the information included in the second data frame.

In the method of operating the electronic device according to various embodiments of the disclosure, the receiving of the UWB signal including the second data frame from the external electronic device may correspond to receiving the UWB signal including the second data frame by using multiple antennas included in the antenna module and may further include identifying direction information of the external electronic device by using information on a time at which the UWB signal including the second data frame is received using the multiple antennas.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 140) including one or more instructions that are stored in a storage medium (e.g., an internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities, and some of the multiple entities may be separately disposed in different components. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
an antenna array;
a communication circuit configured to control the antenna array; and
at least one processor operatively connected to the communication circuit,
wherein the at least one processor is configured to:
transmit an ultra-wide band (UWB) signal including a first data frame to an external electronic device,
receive, based on the transmitted first data frame, a reflected first data frame,
obtain a first channel impulse response based on the reflected first data frame,
acquire information based on the first channel impulse response, and
receive an UWB signal including a second data frame from the external electronic device in response to the transmitted first data frame.

2. The electronic device of claim 1, wherein the at least one processor is further configured to configure a reception antenna of the antenna array to be turned on, before transmitting the UWB signal including the first data frame.

3. The electronic device of claim 2, wherein the at least one processor is further configured to configure the reception antenna to be turned off when a maximum allowable time to receive the reflected first data frame has passed.

4. The electronic device of claim 1, wherein the at least one processor is further configured to determine to enable an UWB ranging mode and a radar mode at the same time based on a state of the electronic device before transmitting the UWB signal including the first data frame.

5. The electronic device of claim 4, wherein the at least one processor is further configured to select a data frame element from among a plurality of data frame elements of the first data frame for radar mode operation.

6. The electronic device of claim 5, wherein the selected data frame element corresponds to a synchronizer (SYNC) and a scrambled timestamp secure (STS).

7. The electronic device of claim 1, wherein the at least one processor is further configured to:
transmit an UWB signal including a third data frame to the external electronic device in response to the second data frame,
receive, based on the transmitted third data frame, a reflected third data frame,
obtain a second channel impulse response based on the reflected third data frame, and
acquire information, based on the first channel impulse response and the second channel impulse response.

8. The electronic device of claim 1, wherein the information acquirable based on the first channel impulse response corresponds to one of existence or absence of a living thing, a heart rate, and a movement of an object.

9. The electronic device of claim 1,
wherein the second data frame comprises information about a time at which the external electronic device has received the first data frame and a time at which the external electronic device transmits the second data frame,
wherein the at least one processor is further configured to calculate a distance between the electronic device and the external electronic device based on a transmission time of the first data frame, and
wherein the transmission time of the first data frame is based on a difference between the time at which the electronic device transmits the first data frame and the time at which the external electronic device has received the first data frame included in the second data frame.

10. The electronic device of claim 1,
wherein the antenna array comprises multiple antennas, and
wherein the at least one processor is further configured to:
receive the UWB signal including the second data frame by the multiple antennas, and
identify direction information of the external electronic device based on a time at which the UWB signal including the second data frame is received by the multiple antennas.

11. A method of operating an electronic device, the method comprising:
transmitting an ultra-wide band (UWB) signal including a first data frame to an external electronic device;
receiving, based on the transmitted first data frame, a reflected first data frame;
obtaining a first channel impulse response based on the reflected first data frame;
acquiring information based on the first channel impulse response; and
receiving an UWB signal including a second data frame from the external electronic device in response to the transmitted first data frame.

12. The method of claim 11, further comprising:
configuring a reception antenna to be turned on, before transmitting the UWB signal including the first data frame.

13. The method of claim 12, further comprising:
configuring the reception antenna to be turned off when a maximum allowable time to receive the reflected first data frame has passed.

14. The method of claim 13,
wherein the configuring the reception antenna to be turned off is performed before the receiving of the UWB signal including the second data frame from the external electronic device.

15. The method of claim 11, further comprising:
determining to enable an UWB ranging mode and a radar mode at the same time based on a state of the electronic device before transmitting the UWB signal including the first data frame.

16. The method of claim 15, further comprising:
selecting a data frame element from among a plurality of data frame elements of the first data frame for radar mode operation.

17. The method of claim 16, wherein the selected data frame element corresponds to a synchronizer (SYNC) and a scrambled timestamp secure (STS).

18. The method of claim 11, further comprising:
transmitting an UWB signal including a third data frame to the external electronic device in response to the second data frame;
receiving, based on the transmitted third data frame, a reflected third data frame;
obtaining a second channel impulse response based on the reflected third data frame; and
acquiring information, based on the first channel impulse response and the second channel impulse response.

19. The method of claim 11, wherein the information acquirable based on the first channel impulse response corresponds to one of existence or absence of a living thing, a heart rate, and a movement of an object.

20. The method of claim 11,
wherein the second data frame comprises information about a time at which the external electronic device has received the first data frame and a time at which the external electronic device transmits the second data frame,
wherein the method further comprises calculating a distance between the electronic device and the external electronic device based on a transmission time of the first data frame, and
wherein the transmission time of the first data frame is based on a difference between the time at which the electronic device transmits the first data frame and the time at which the external electronic device has received the first data frame included in the second data frame.

21. The method of claim 11,
wherein the receiving of the UWB signal including the second data frame from the external electronic device comprises receiving the UWB signal including the second data frame by multiple antennas, and
wherein the method further comprises identifying direction information of the external electronic device based on a time at which the UWB signal including the second data frame is received by the multiple antennas.

* * * * *